US007957566B2

(12) United States Patent
Suzuki et al.

(10) Patent No.: US 7,957,566 B2
(45) Date of Patent: Jun. 7, 2011

(54) EYELID DETECTION APPARATUS, EYELID DETECTION METHOD AND PROGRAM THEREFOR

(75) Inventors: Tomoharu Suzuki, Anjo (JP); Takashi Hiramaki, Nagoya (JP); Jun Adachi, Obu (JP); Kenichi Ohue, Toyota (JP); Yuji Ninagawa, Aichi-ken (JP); Kentaro Takahashi, Toyota (JP); Shigeyasu Uozumi, Toyota (JP); Satoru Nakanishi, Aichi-ken (JP); Shinichi Kojima, Nisshin (JP)

(73) Assignees: Aisin Seiki Kabushiki Kaisha, Aichi-ken (JP); Toyota Jidosha Kabushiki Kaisha, Aichi-ken (JP)

( * ) Notice: Subject to any disclaimer, the term of this patent is extended or adjusted under 35 U.S.C. 154(b) by 696 days.

(21) Appl. No.: 12/047,612

(22) Filed: Mar. 13, 2008

(65) Prior Publication Data
US 2008/0226139 A1 Sep. 18, 2008

(30) Foreign Application Priority Data
Mar. 15, 2007 (JP) ................................. 2007-066780

(51) Int. Cl.
*G06K 9/00* (2006.01)
(52) U.S. Cl. .................................................. 382/117
(58) Field of Classification Search .................. 382/116, 382/117
See application file for complete search history.

(56) References Cited

U.S. PATENT DOCUMENTS 5,805,720 A * 9/1998 Suenaga et al. ............... 382/117
7,426,287 B2 * 9/2008 Yoon et al. .................... 382/118
2005/0063568 A1 * 3/2005 Sun et al. ...................... 382/117
2006/0098867 A1   5/2006 Gallagher
2006/0291702 A1 * 12/2006 Miessbacher ................. 382/117

FOREIGN PATENT DOCUMENTS

| EP | 1 669 909 A1 | 6/2006 |
| JP | 2000-123148 A | 4/2000 |
| JP | 2000-137792 A | 5/2000 |
| JP | 2000-311248 A | 11/2000 |

OTHER PUBLICATIONS

Japanese Office Action dated Feb. 3, 2009, with translation (14 pages).
European Search Report dated Mar. 8, 2010 (6 pages).
Sohail, Abu Sayeet Md., et al., "Classifying facial expressions using point-based analytic face model and Support Vector Machines," Systems, Man and Cybernetics, 2007 ISIC, IEEE International Conference on, IEEE, PI, Oct. 10, 2007, pp. 1008-1013.

* cited by examiner

*Primary Examiner* — Matthew C Bella
*Assistant Examiner* — Dennis Rosario
(74) *Attorney, Agent, or Firm* — Sughrue Mion, PLLC

(57) ABSTRACT

An eyelid detection apparatus includes a face-image storing apparatus for storing an image of a face of a subject, an eyelid-candidate extracting apparatus for processing the image stored in the face-image storing apparatus to extract a pair of lines, which becomes a candidate of a combination of a line corresponding to an upper eyelid and a line corresponding to a lower eyelid, a parameter calculating apparatus for calculating a parameter, which indicates a possibility that a pan of the image stored in the face-image storing apparatus, the part corresponding to the pair of lines extracted by the eyelid-candidate extracting apparatus, includes at least one of outer and inner corners of an eye, and an eyelid detecting apparatus for detecting a position of an eyelid of the subject on the basis of the parameter calculated by the parameter calculating apparatus.

6 Claims, 15 Drawing Sheets

FIG. 3A
Vertical-edge detecting operator
| -1 | 0 | 1 |
|---|---|---|
| -2 | 0 | 2 |
| -1 | 0 | 1 |
FIG. 3B
Horizontal-edge detecting operator
| -1 | -2 | -1 |
|---|---|---|
| 0 | 0 | 0 |
| 1 | 2 | 1 |
FIG. 3C
FIG. 3D
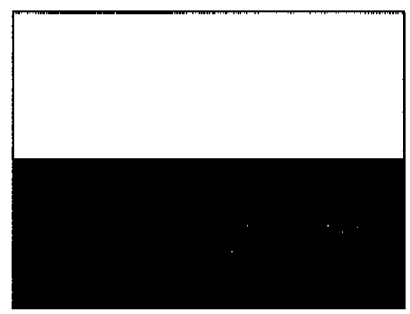
FIG. 3E
Left end pattern of
outer or inner corner of eye
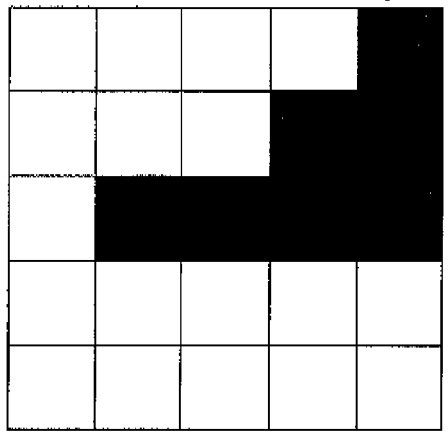
FIG. 3F
Right end pattern of
outer or inner corner of eye
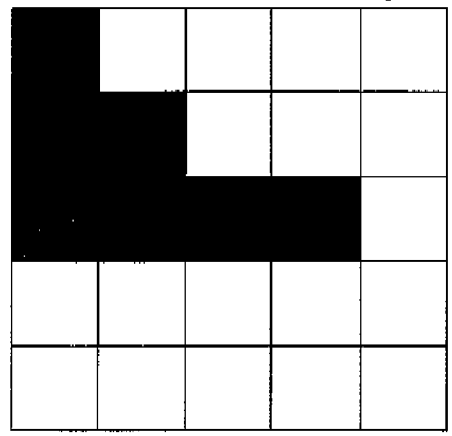

FIG. 4

Parameters utilized in eyelid detection process

| Parameter name | Value |
|---|---|
| Eyelid detecting horizontal Sobel threshold | 8 |
| Eyelid-region setting parameter $a (= n - w)$ | 9 |
| Eyelid-region setting parameter $b (= v - m)$ | 6 |
| Threshold $Lth$ | 2 |
| Threshold $Cxth$ | 2 |
| Threshold $Dth$ | 2 |

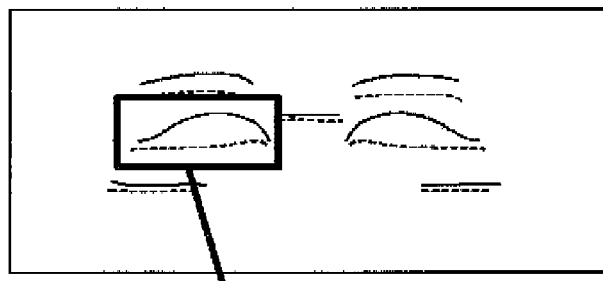
FIG.14A
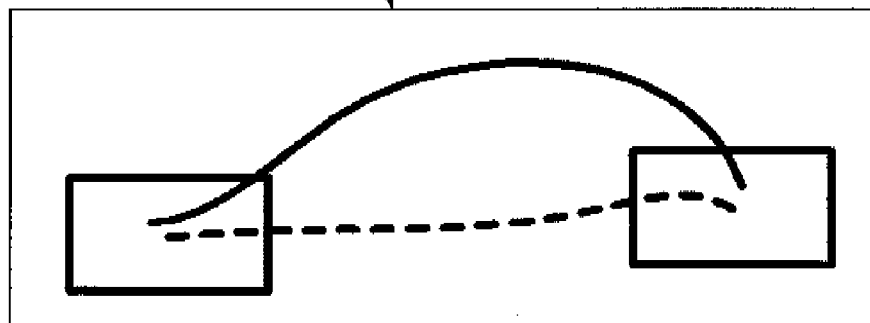
FIG.14B
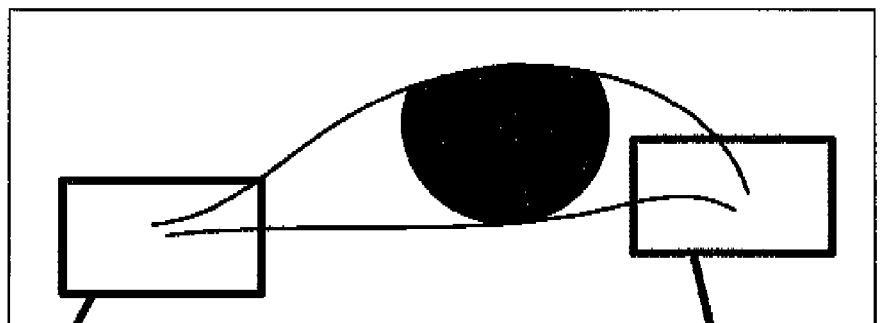
FIG.14C
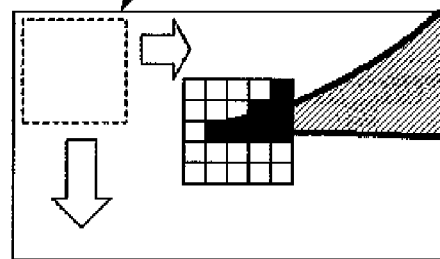 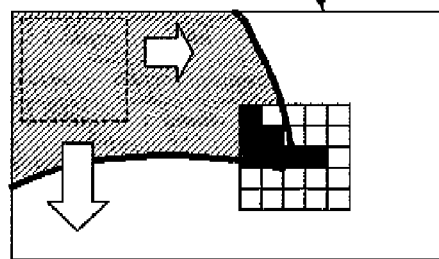
FIG.14D  FIG.14E

EYELID DETECTION APPARATUS, EYELID DETECTION METHOD AND PROGRAM THEREFOR

CROSS REFERENCE TO RELATED APPLICATIONS

This application is based on and claims priority under 35 U.S.C. §119 to Japanese Patent Application 2007-066780, filed on Mar. 15, 2007, the entire content of which is incorporated herein by reference.

FIELD OF THE INVENTION

This invention generally relates to an eyelid detection apparatus, an eyelid detection method and a program therefor.

BACKGROUND

A technique for detecting a position of a face or an eye of a human from an image including the face of the human is known. For example, JP2000-137792A describes a technique for continuously and correctly detecting an eye by extracting an edge line corresponding to an upper eyelid and an edge line corresponding to a lower eyelid from a face image, by generating a template thereof and matching the template to a candidate of the eye.

However, in the technique of JP2000-137792A, correlative operation is performed for matching the template. Accordingly, a processing time tends to be long. Therefore, the operation of the technique of JP2000-133792A is difficult for an in-vehicle CPU, of which a processing speed is low. Further, using a dedicated computing unit tends to cause high cost.

A need thus exists for an eyelid detection apparatus, an eyelid detection method and a program therefor which is not susceptible to the drawback mentioned above.

SUMMARY OF THE INVENTION

According to an aspect of the present invention, an eyelid detection apparatus includes a face-image storing means for storing an image of a face of a subject, an eyelid-candidate extracting means for processing the image stored in the face-image storing means to extract a pair of lines, which becomes a candidate of a combination of a line corresponding to an upper eyelid and a line corresponding to a lower eyelid, a parameter calculating means for calculating a parameter, which indicates a possibility that a part of the image stored in the face-image storing means, the part corresponding to the pair of lines extracted by the eyelid-candidate extracting means, includes at least one of outer and inner corners of an eye, and an eyelid detecting means for detecting a position of an eyelid of the subject on the basis of the parameter calculated by the parameter calculating means.

According to another aspect of the present invention, an eyelid detection method includes processes of processing a face image to extract a pair of lines, which becomes a candidate of a combination of an upper eyelid and a lower eyelid, calculating a parameter which indicates a possibility that the extracted pair of lines which becomes the candidate of the combination of the upper eyelid and the lower eyelid, includes at least one of outer and inner corners of an eye, and detecting a position of an eyelid of a subject on the basis of the calculated parameter.

According to another aspect of the present invention, a program instructs a computer to function as a face-image storing means for storing an image of a face of a subject, an eyelid candidate-extracting means for processing the image stored in the face-image storing means and extracting a pair of lines which becomes a candidate of a combination of a line corresponding to an upper eyelid and a line corresponding to a lower eyelid, a parameter calculating means for calculating a parameter which indicates possibility that a part of the image stored in the face-image storing means, the part corresponding to the pair of lines extracted by the eyelid-candidate extracting means, includes at least one of outer and inner corners of an eye, and an eyelid detecting means for detecting a position of an eyelid of the subject on the basis of the parameter calculated by the parameter calculating means.

BRIEF DESCRIPTION OF THE DRAWINGS

The foregoing and additional features and characteristics of the present invention will become more apparent from the following detailed description considered with reference to the accompanying drawings, wherein:

FIG. 3A to FIG. 3F represent explanatory diagrams illustrating data stored in a ROM or a RAM;

FIG. 4 represents an explanatory diagram illustrating data stored in the ROM or the RAM;

FIG. 14A to FIG. 14B represent explanatory diagrams illustrating an outline of an eyelid detection process of a second embodiment.

DETAILED DESCRIPTION (First embodiment) A eyelid detection apparatus 50 according to a first embodiment of the present invention will be explained wit reference to drawing figures.

Figure 1:
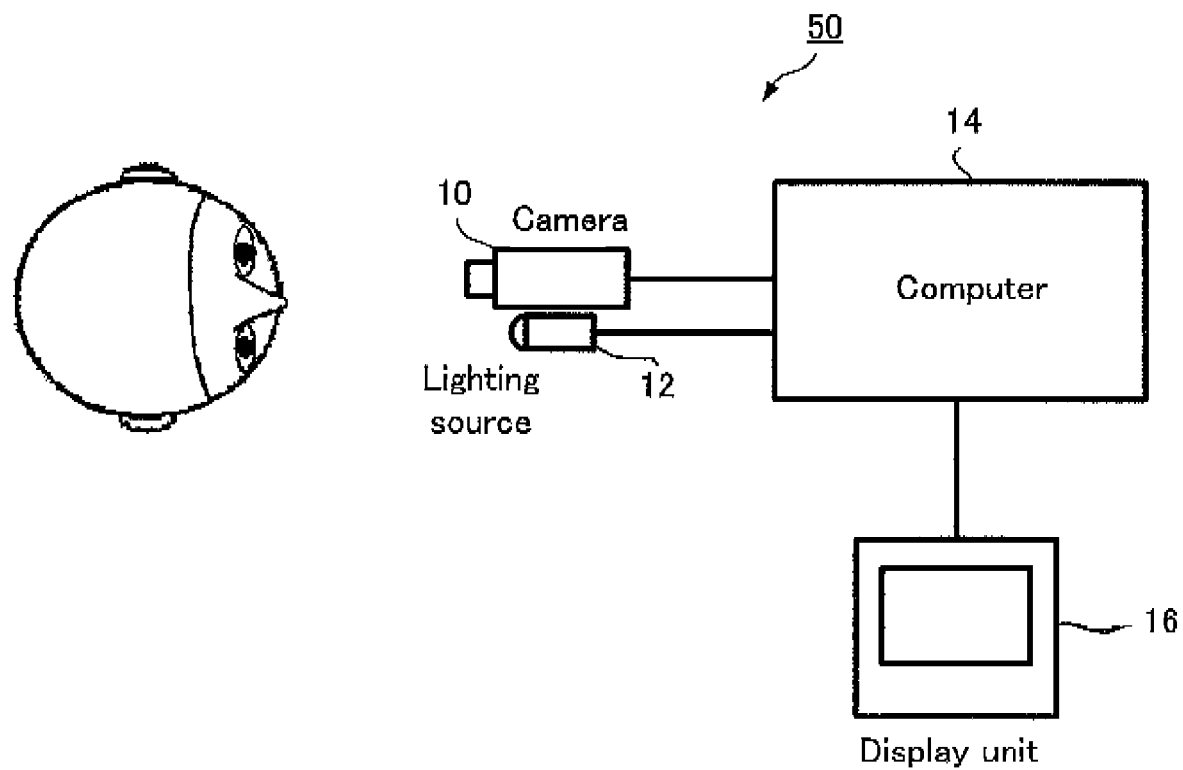
FIG. 1 represents a block diagram illustrating a configuration of an eyelid detection apparatus according to a first embodiment of the present invention.

As illustrated in FIG. 1, the eyelid detection apparatus 50 according to the first embodiment includes a camera 10 for taking an image of a face of a driver and generating a face image, a lighting source 12 for lighting the face of the driver, a computer 14 for detecting an eyelid of the driver and a display unit 16 connected to the computer 14.

The camera 10 is composed of a CCD camera, or the like. The camera 10 takes a gray-scale image of the face of the driver at a predetermined cycle (for example, 1/30 seconds) and outputs the gray-scale image of the face of the driver. The face image sequentially output from the camera 10 includes, not only the image of the face of the driver, but also a background image.

The display unit 16 is composed oft for example, a liquid crystal display (LCD) or a cathode ray tube (CRT), or the like. The display unit 16 displays a binarized image generated from the face image taken by the camera 10, or the like.

Figure 2:
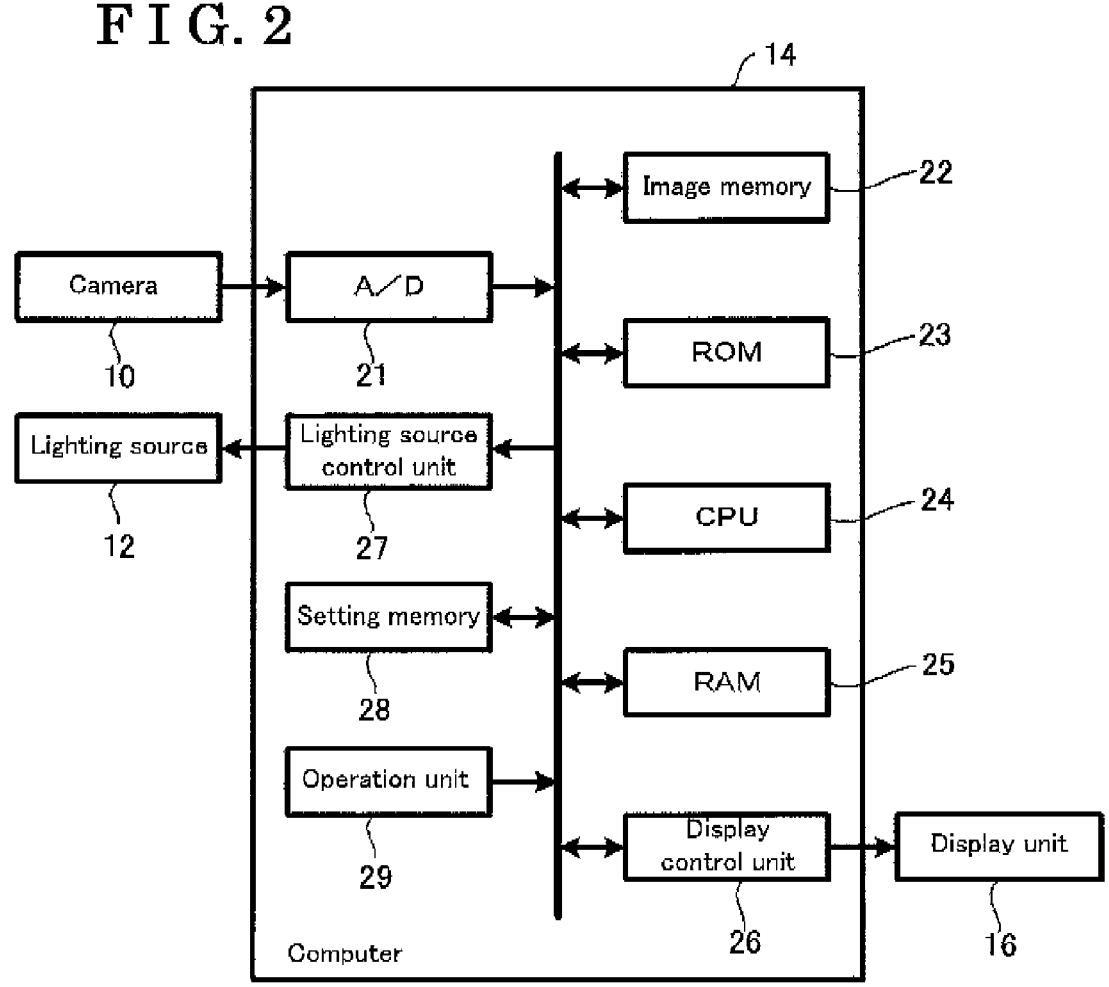
FIG. 2 represents a block diagram illustrating a configuration of a computer illustrated in FIG. 1.

The computer 14 processes a motion image of the face taken by the camera 10 to detect a position of the eyelid. As illustrated in FIG. 2, the computer 14 is composed of an analog-digital (A/D) converter 21, an image memory 22, a read only memory (ROM) 23 (pattern storing means), a central processing unit (CPU) 24, a random access memory (RAM) 25, a display control unit 26, a lighting source control unit 27, a setting memory 28 and an operation unit 29.

The A/D (analog-digital) converter 21 converts an analog image signal taken by the camera 10 into a digital signal.

The image memory 22 (face-image storing means) is generated by tie camera 10 and stores an image data digitized by the A/D converter 21.

The ROM 23 stores a program for controlling a CPU operation. Further, the ROM 23 stores various kinds of fixed data for executing an image process described below.

The CPU 24 controls the compute 14. Further, the CPU 24 executes the programs stored in the ROM 23 to process a series of the face images taken by the camera 10 and to detect the eyelid. The CPU 24 serves as an eyelid-candidate extracting means for performing an eyelid-candidate extracting process (S300), a parameter calculating means for performing a parameter calculating process (S440), an eyelid detecting means for performing an eyelid detecting process (S470). Further, the CPU 24 serves as a difference calculating means for performing a difference calculating process (S550).

The RAM 25 functions as a work area of the CPU 24.

The display control unit 26 converts the image data, or the like, into a data format, which can be output by the display unit 16, under the control of the CPU 24 and outputs the converted data to the display unit 16.

The lighting source control unit 27 controls turning on and off of the lighting source 12.

The setting memory 28 preliminarily stores parameters illustrated in FIG. 4. The parameters are utilized when the CPU 24 detects the eyelid from the face image stored in the RAM 25. Details will be described below.

The operation unit 29 receives an operation request from a user and sends an operation signal corresponding to the requested operation to the CPU 24.

Next, an example of the fixed data stored in the ROM 23 will be described with reference to FIGS. 3A to 3F. Firstly, as illustrated in FIG. 3A, the ROM 23 stores a vertical-edge detecting operator (vertical-edge detecting Sobel filter). The vertical-edge detecting Sobel filter is an operator for emphasizing a gray level difference in a horizontal direction as illustrated in FIG. 3C.

Further, the ROM 23 stores a horizontal-edge detecting operator (horizontal-edge detecting Sobel filter). The horizontal-edge detecting Sobel filter is an operator for emphasizing a gray level difference in a vertical direction as illustrated in FIG. 3D.

The ROM 23 stores a left end pattern of an outer or inner corner of an eye as illustrated in FIG. 3E. The left end pattern of the outer or inner corner of the eye is made from an actual image of the outer or inner corner of the eye. The pattern of the outer or inner corner of the eye is composed of a part representing a skin (skin region corresponding to a skin part) around the outer or inner corer of the eye and a part representing the eye (eye region corresponding to an eye part). In the diagram, a white pixel is the part representing the skin and a black pixel is the part representing the eye. The left end pattern of the outer or inner corner of the eye is utilized for judging how an image near a left end of an actual edge line resembles the outer or inner corner of the eye.

The ROM 23 stores a right end pattern of the outer or inner corner of the eye as illustrated in FIG. 3F. The right end pattern of the outer or inner corner of the eye is made from the actual image of the outer or inner corner of the eye. The pattern of the outer or inner corner of the eye includes a part representing the skin (skin region corresponding to the skin part) around the outer or inner corner of the eye and a part representing the eye (eye region corresponding to the eye part). In the diagram, a white pixel is the part representing the skin and a black pixel is the part representing the eye. The right end pattern of the outer or inner corner of the eye is utilized for judging how an image near a right end of the actual edge line resembles the outer or inner corner of the eye.

An example of parameters stored in the setting memory 28 will be explained with reference to FIG. 4. Firstly, an eyelid detecting horizontal Sobel threshold is a threshold utilized when an eyelid region of the face is extracted from the face image for judging whether each pixel is a part of a horizontal edge line or not from an absolute value of each pixel value processed by the horizontal-edge detecting Sobel filter. Eyelid-region setting parameters a and b are parameters for calculating the eyelid regions in which the eyelid is assumed to be present, from a detected face position. Thresholds Lth, Cxth and Dth are thresholds utilized for extracting an edge line pair, which becomes al eyelid candidate.

An operation of the eyelid detection apparatus 50 according to the first embodiment will be described. In the first embodiment, the eyelid detection apparatus 50 is configured as described above.

Firstly; an operation of the eyelid detection apparatus 50 for detecting the eyelid in the face image will be outlined with reference to FIGS. 3A to 3F, FIG. 4, FIGS. 5A to 5D and FIGS. 6A to 6C.

Figure 5A:
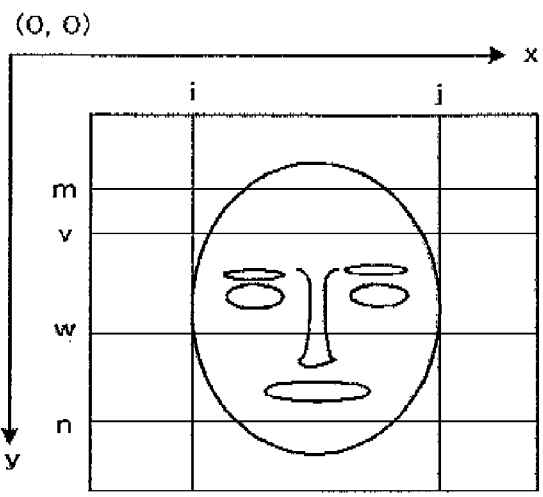
FIG. 5A to FIG. 5D represent explanatory diagrams illustrating an outline of processes according to the first embodiment of the present invention.

The camera 10 takes a face image of a subject, as illustrated in FIG. 5A, at the predetermined cycle (for example, 1/30 seconds) and outputs the face image. The output face image is sequentially stored in the image memory 22.

Next the CPU 24 sequentially loads the face image stored in the image memory 22 and executes following processes.

Firstly, the CPU 24 processes the loaded face image with use of the vertical-edge detecting Sobel filter (FIG. 3A) and detects right ad left ends of the face on the basis of each pixel value of the face image. Further, the CPU 24 processes the loaded face image with use of the horizontal-edge detecting Sobel filter (FIG. 3B) and detects upper and lower ends of the face on the basis of each pixel value of the face image.

For example, in a case of the face image illustrated in FIG. 5A, the right and left ends of the face are x=i, j and the upper and lower ends are y=m, n. The face position can be detected from the right and left ends and the upper and lower ends of the face.

Figure 5B:

The CPU 24 detects the eyelid region, in which the eyelid is assumed to be included, as illustrated in FIG. 5B, on the basis of the parameters stored in the setting memory 23 and the detected face position. Specifically, with reference to FIG. 5A, in a case where the right and left ends of the face are x=i, j and the upper and lower ends are y=m, n, the eyelid region is, with use of the eyelid-region setting parameters a and b stored in the setting memory 28, represented by i≦x≦j and v≦y≦w (where v=m+b, w=n−a).

The CPU 24 performs a process for extracting the horizontal edge line in the image of the eyelid region with use of the horizontal-edge detecting Sobel filter (FIG. 3B). Here, the CPU 24 determines a pixel, of which an absolute value of a derivative value processed with use of the horizontal-edge detecting Sobel filter is equal to or more than the eyelid detecting horizontal Sobel threshold (FIG. 4), as the part of the horizontal edge line.

Figure 5C:
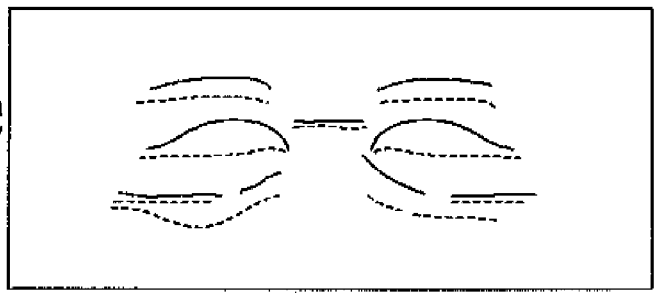

As a result, as illustrated in FIG. 5C, an edge line, across which a brightness of a pixel changes from bright to dark in a y-axis direction, is exhibited as a minus edge. An edge line, across which the brightness of a pixel changes from dark to bright in the y-axis direction, appears as a plus edge. In the meantime, the minus edge is represented by a solid line and the plus edge is represented by a dashed line in the figure.

Next, the CPU 24 extracts a combination (edge line pair) of the minus edge and the plus edge, which satisfy following three formulas, from the obtained minus edges and the plus edges, as a candidate of upper and lower eyelids.

$$Lp-Lm<Lth \quad (1)$$

Here, Lp is a value indicating a length of the plus edge, Lm is a value indicating a length of the minus edge, and Lth indicates the threshold. The threshold Lth is stored in the setting memory 28 as illustrated in FIG. 4. The lengths of the minus edge and the plus edge, which satisfy the formula (1), are approximate to each other, where a difference therebetween is within the threshold Lth.

$$Cxp-Cxm<Cxth \quad (2)$$

Here, Cxp indicates an x-coordinate of a centroid of the plus edge, Cxm indicates an x-coordinate of a centroid of the minus edge, and Cxth indicates the threshold. The threshold Cxth is stored in the setting memory 28 as illustrated in FIG. 4. The x-coordinates of the centroids of the minus edge and the plus edge, which satisfy the formula (2), are approximate to each other, where a difference therebetween is within the threshold Cxth.

$$Dg<Dth \quad (3)$$

Here, Dg indicates a distance between the centroids of the plus edge and the minus edge and Dth indicates tie threshold. The threshold Dth is stored in the setting memory 28 as illustrated in FIG. 4. The distance between the centroids of the minus edge and the plus edge, which satisfies the formula (3), is within the threshold Dth.

In the combination of the minus edge and the plus edge, which is extracted by the CPU 24 with use of the three formulas described above, the minus edge is considered as an upper eyelid candidate and the plus edge is considered as a lower eyelid candidate.

In other words, when the combination of the minus edge and the plus edge satisfies the formulas (1) to (3), the lengths of the minus edge and the plus edge are equal to each other to some extent, the positions of the minus edge and the plus edge are close to each other to some extent and the x-coordinates of the centroids of the minus edge and the plus edge correspond to to some extent.

Figure 5D:
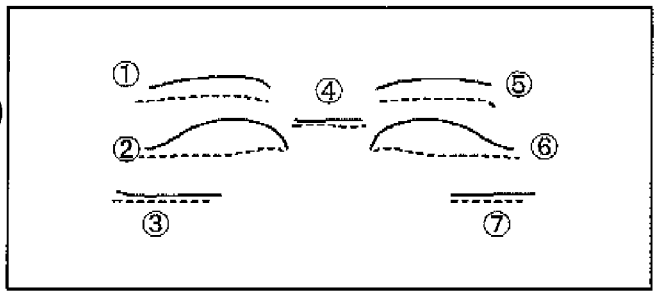

FIG. 5D represents a diagram illustrating an example of a combination of the minus edge and the plus edge extracted with use of the formulas (1) to (3). Candidates 1 to 7, which are combinations of the plus edge and the minus edge, are eyelid candidates of the subject (edge line pair).

Figure 6A:
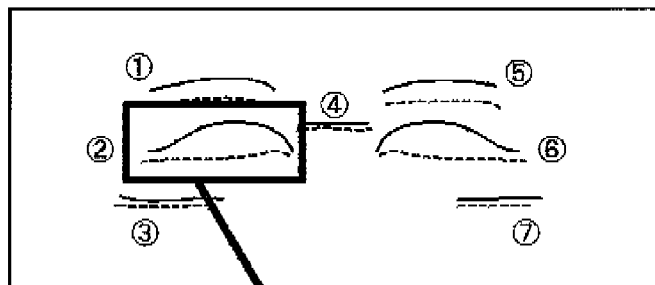
FIG. 6A to FIG. 6C represent explanatory diagrams illustrating the outline of the processes according to the first embodiment of the present invention.
Figure 6B:
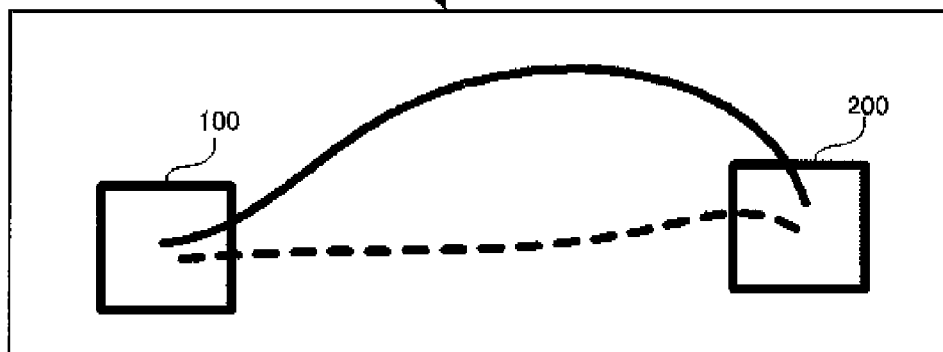

Next, the CPU 24 sets a region of the outer or inner corner of the eye at right and left ends of each eyelid candidate (edge line pair). The region of the outer or inner corner of the eye is a region, in which a possibility of existence of the outer or inner corner of the eye is high. In the embodiment, the region of the outer or inner corner of the eye is a region of 5 pixels (horizontal)×5 pixels (vertical) set at each of right and left ends of the lower eyelid candidate (plus edge) of the eyelid candidate (edge line pair) as a center. For example, as illustrated in FIGS. 6A and 6B, for the eyelid candidate 2, the region 100 of the outer or inner corner of the eye and the region 200 of the outer or inner corner of the eye are set at the left and right ends of the lower eyelid candidate (plus edge).

The CPU 24 calculates a left end evaluation value of the outer or inner corner of the eye with use of the left end pattern of the outer or inner corner of the eye (FIG. 3E) for the region of the outer or inner corner of the eye set at a left end of the plus edge of each set eyelid candidate as a center. Further, the CPU 24 calculates a right end evaluation value of the outer or inner corner of the eye with use of the right end pattern of the outer or inner corner of the eye (FIG. 3F) for the region of the outer or inner corner of the eye set at a right end of the plus edge of each set eyelid candidate as a center.

Figure 6C:
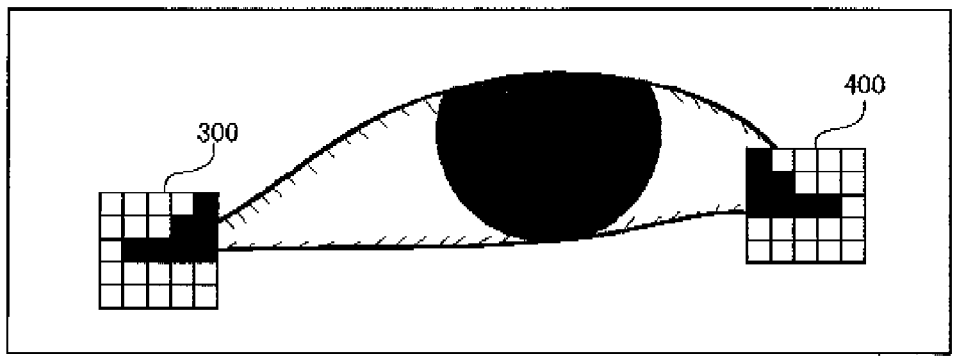

Specifically, as illustrated in FIG. 6C, the CPU 24 locates the pattern of the outer or inner corner of the eye on an original image before the Sobel filter process at a region corresponding to the region of the outer or inner corner of the eye. Next, the CPU 24 calculates an average value of intensity of pixels in the original image at a part corresponding to a skin part of the pattern and an average value of intensity of pixels in the original image at a part corresponding to an eye part of the pattern. The CPU 24 calculates an evaluation value (parameter, difference) of the outer or inner corner of the eye by subtracting the calculated average of the intensity of the pixels in the original image at the part corresponding to the eye part from the calculated average of the intensity of the pixels in the original image at the part corresponding to the skin part. The CPU 24 calculates two evaluation values of the outer and inner corners of the eye for the right and left ends of each eyelid candidate (edge line pair).

The CPU 24 calculates a summation of the left end evaluation value of the outer or inner corner of the eye and the right end evaluation value of the outer or inner corner of the eye of each eyelid candidate. The CPU 24 determines a largest summation of the right end and left end evaluation values of the outer or inner corner of the eye as right or left eyelid. The CPU 24 can determine the largest summation of the right end and left end evaluation values of the outer or inner corner of the eye and a second largest summation of the right end and left end evaluation values of the outer or inner corner of the eye as right and left eyelids.

Details of the operation of the eyelid detection apparatus 50 for detecting the eyelid in the face image will be explained with reference to from FIG. 7 to FIG. 13.

An eyelid detection process performed by the eyelid detection apparatus 50 according to the first embodiment of the present invention will be explained with reference to a flowchart illustrated in FIG. 7.

Figure 7:
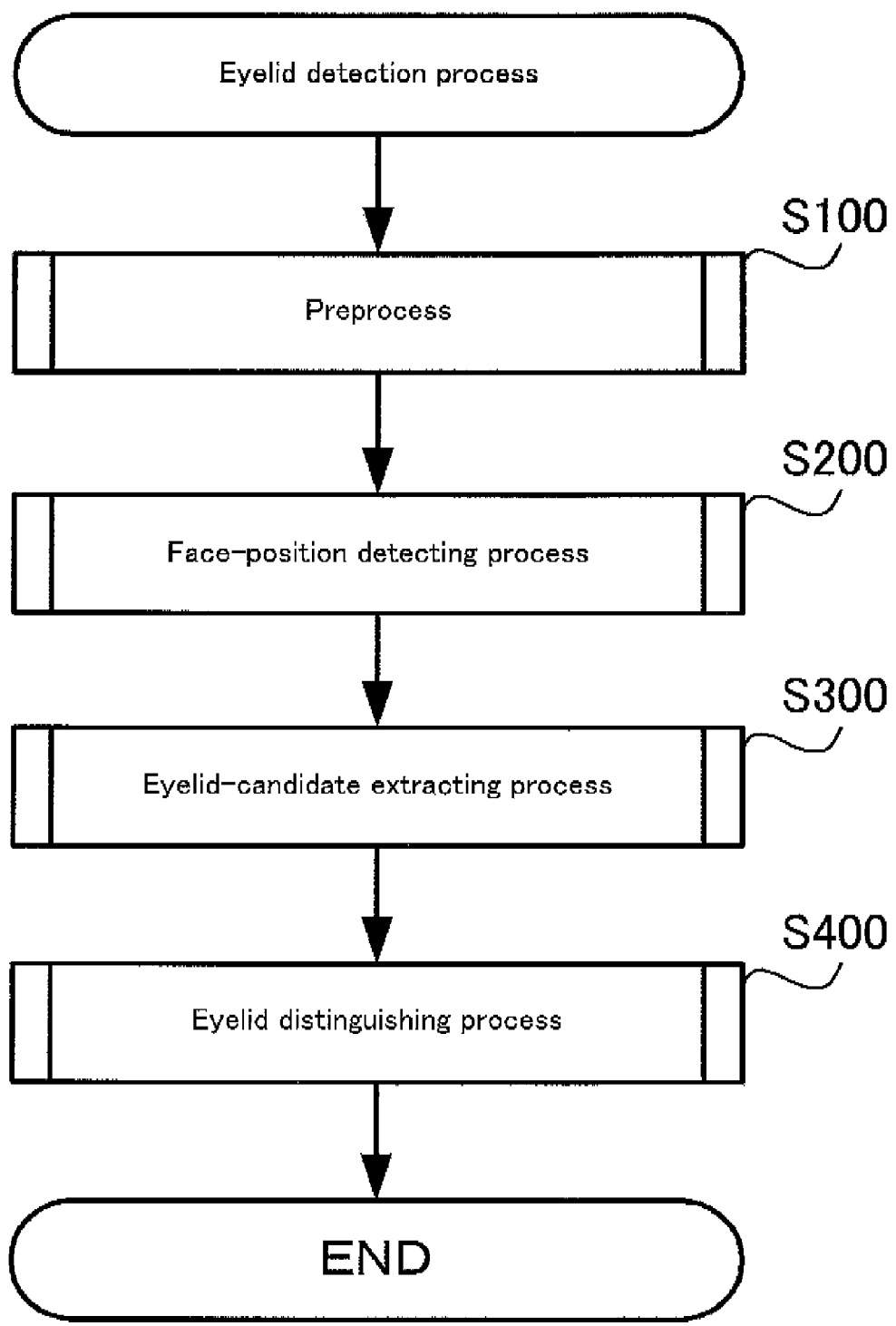
FIG. 7 represents an explanatory diagram illustrating a flowchart of an eyelid detection process according to the first embodiment of the present invention.

The CPU 24 in the computer 14 periodically (for example, every 1/30 seconds) starts the eyelid detection process illustrated in FIG. 7.

Firstly, power of the eyelid detection apparatus 50 is turned on. Then, the CPU 24 performs a preprocess described below. The CPU 24 takes the face image of the driver, extracts a vertical edge line, and extracts the horizontal edge line (step S100).

Next, the CPU 24 performs a face-position detecting process described below. The CPU 24 detects the right and left ends of the face with use of the vertical edge line extracted in the preprocess described above, detects the upper and lower ends of the face with use of the horizontal edge line extracted in the preprocess described above, and detects the face position in the face image (step S200).

The CPU 24 performs an eyelid-candidate extracting process described below. The CPU 24 extracts the eyelid region from the face image with use of the face position detected in the face-position detecting process described above, extracts the horizontal edge lines, extracts a pair of edge lines (edge line pair), which becomes the candidate of the upper and lower eyelids, from the extracted horizontal edge lines (step S300).

The CPU 24 performs an eyelid distinguishing process described below. The CPU 24 sets the region of the outer or inner corner of the eye at the right and left ends of each eyelid candidate, calculates evaluation values of the outer or inner corner of the eye of the set regions and determines the right or left eyelid on the basis of the calculated evaluation values of the outer or inner corner of the eye (step S400). Here, it is possible for the CPU 24 to determine the right and left eyelids on the basis of the calculated evaluation values. Then, the CPU 24 ends the processes.

Thus, according to the eyelid detection process, taking the face image and detecting the eyelid from the image can be periodically repeated.

Next, the preprocess performed in the step S100 of the eyelid detection process will be explained. Briefly, in the preprocess, the eyelid detection apparatus 50 takes the face image of the driver and performs an edge detection with use of a Sobel filter.

Figure 8:
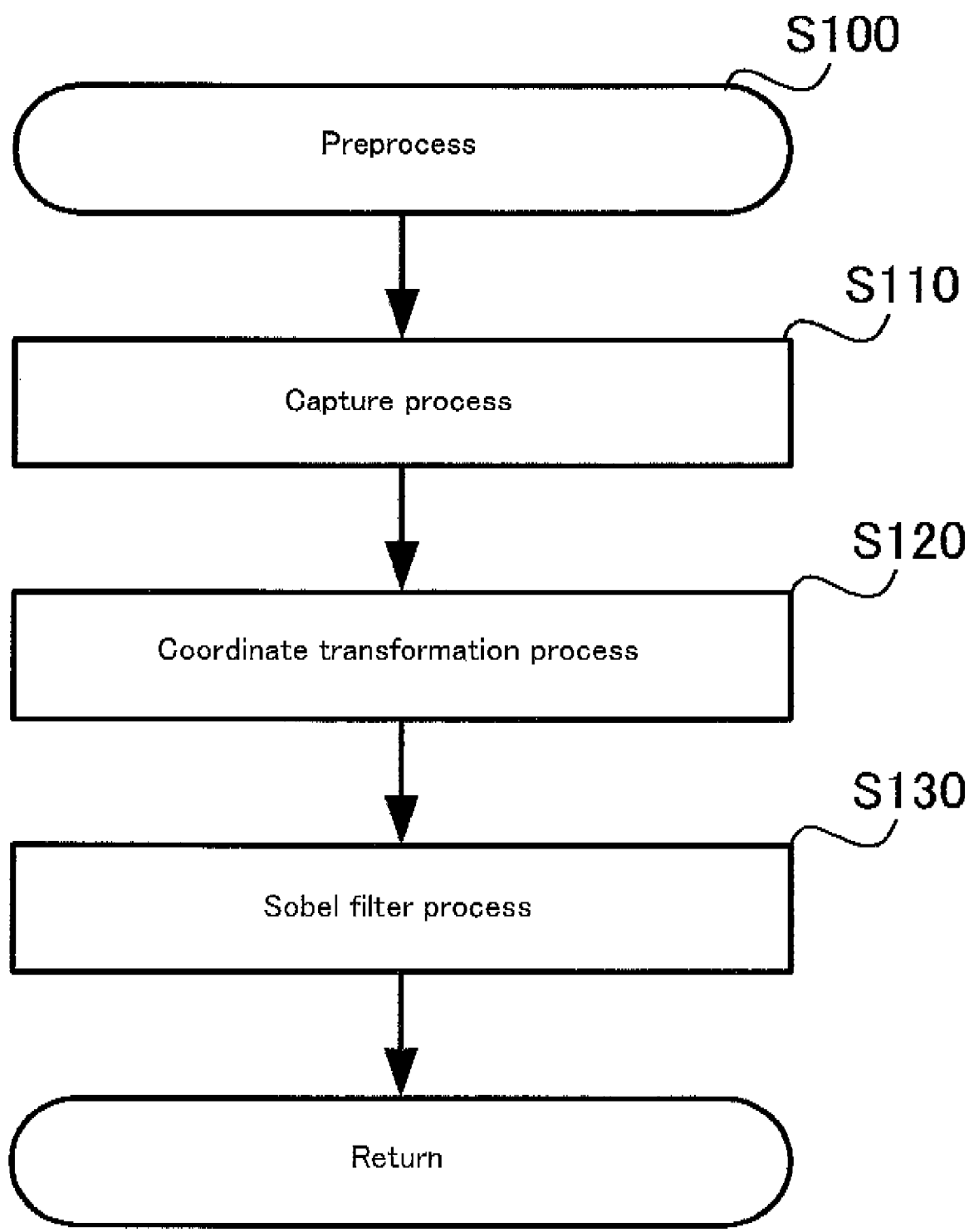
FIG. 8 represents an explanatory diagram illustrating a flowchart of a preprocess in the eyelid detection process of the first embodiment.

The preprocess (S100) will be detailed with reference to FIG. 8.

Firstly, the CPU 24 performs a capture process (step S110). The CPU 24 loads the face image of the subject taken by the camera 10 through the A/D converter 21 and stores the face image in the image memory 22.

Next, the CPU 24 performs a coordinate transformation process. The CPU 24 thins out the pixels of each face image stored in the image memory 22 to a degree that the Sobel filter process described below can be executed (step S120).

The CPU 24 processes the face image after the coordinate transformation with use of the vertical-edge detecting operator (FIG. 3A) stored in the ROM 23 and generates an image, in which the vertical edge line in the face image is emphasized. Further, the CPU 24 processes the face image after the coordinate transformation with use of the horizontal-edge detecting operator (FIG. 3B) stored in the ROM 23 and generates an image, in which the horizontal edge line in the face image is emphasized (step S130).

Thus, according to the preprocess, the image, in which vertical edge line in the taken face image is emphasized, and the image, in which the horizontal edge line in the taken face image is emphasized, can be generated.

Here, the face-position detecting process performed in the step S200 of the eyelid detection process will be explained. Briefly, in the face-position detecting process, the eyelid detection apparatus 50 detects the face position in the face image with use of the image, in which the vertical edge line is emphasized, and the image, in which the horizontal edge line is emphasized, generated in the preprocess.

Figure 9:
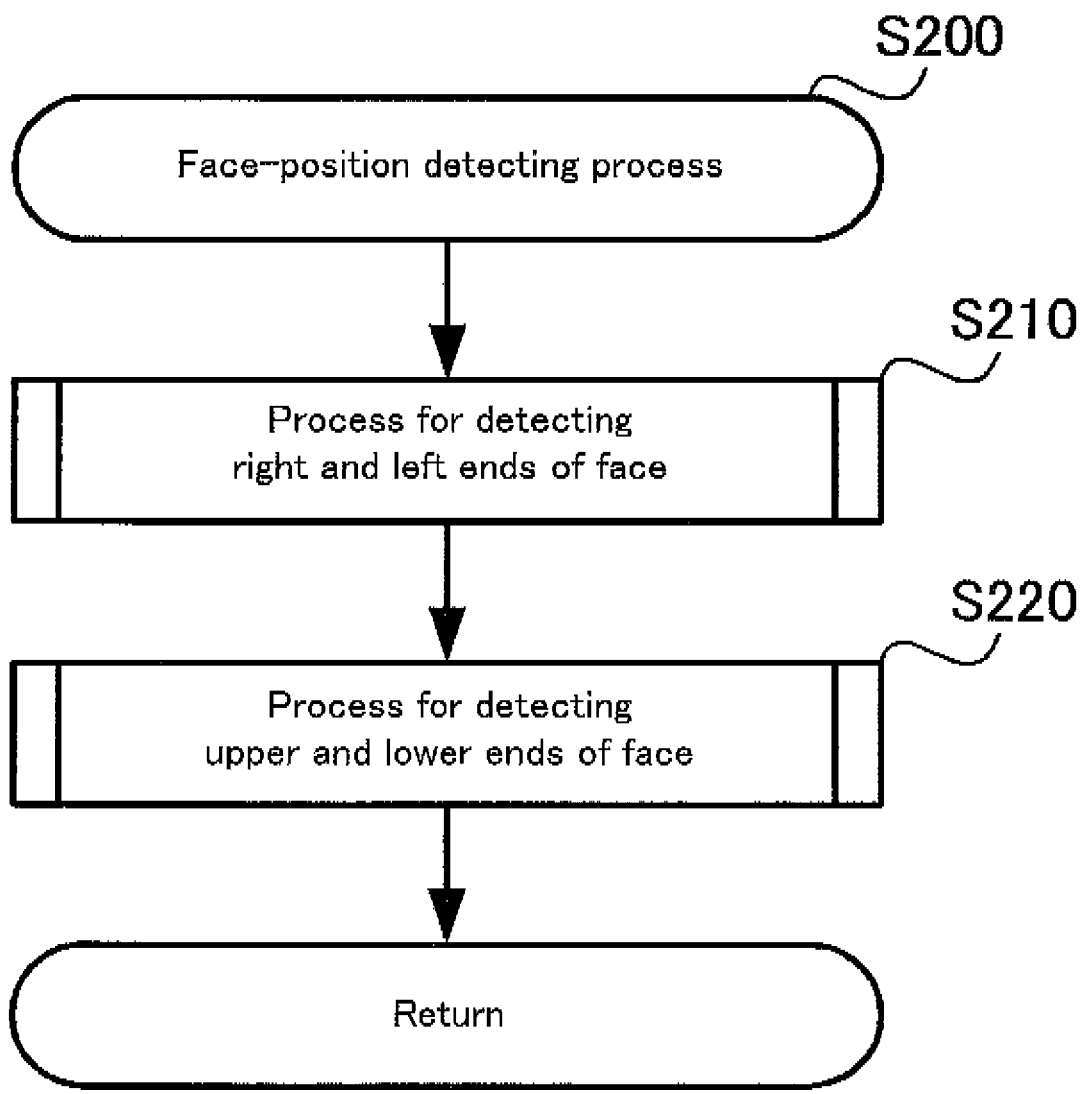
FIG. 9 represents an explanatory diagram illustrating a flowchart of a face-position detecting process in the eyelid detection process of the first embodiment.

Details of the face-position detecting process (S200) will be explained with reference to FIG. 9.

Firstly, the CPU 24 performs a process for detecting the right and left ends of the face described below. The CPU 24 detects a position of the right and left ends of the face in the face image with use of the image, in which the vertical edge line is emphasized, generated in the preprocess (step S210).

Next, the CPU 24 performs a process for detecting the upper and lower ends of the face described below. The CPU 24 detects positions of the upper and lower ends of the face in the face image with use of the image, in which the horizontal edge line is emphasized, generated in the preprocess (step S220). Then, the CPU 24 ends the face-position detecting process.

Thus, according to the face-position detecting process, the face position in the face image can be detected by detecting the right and left ends and the upper and lower ends of the face.

Here, the process for detecting the right and left ends of the face performed in the step S210 of Me face-position detecting process will be explained. Briefly, in the process for detecting the right and left ends of the face, the eyelid detection apparatus 50 detects the position of the right and left ends of the face in the face image with use of the image, in which the vertical edge line is emphasized, generated in the preprocess.

Figure 10:
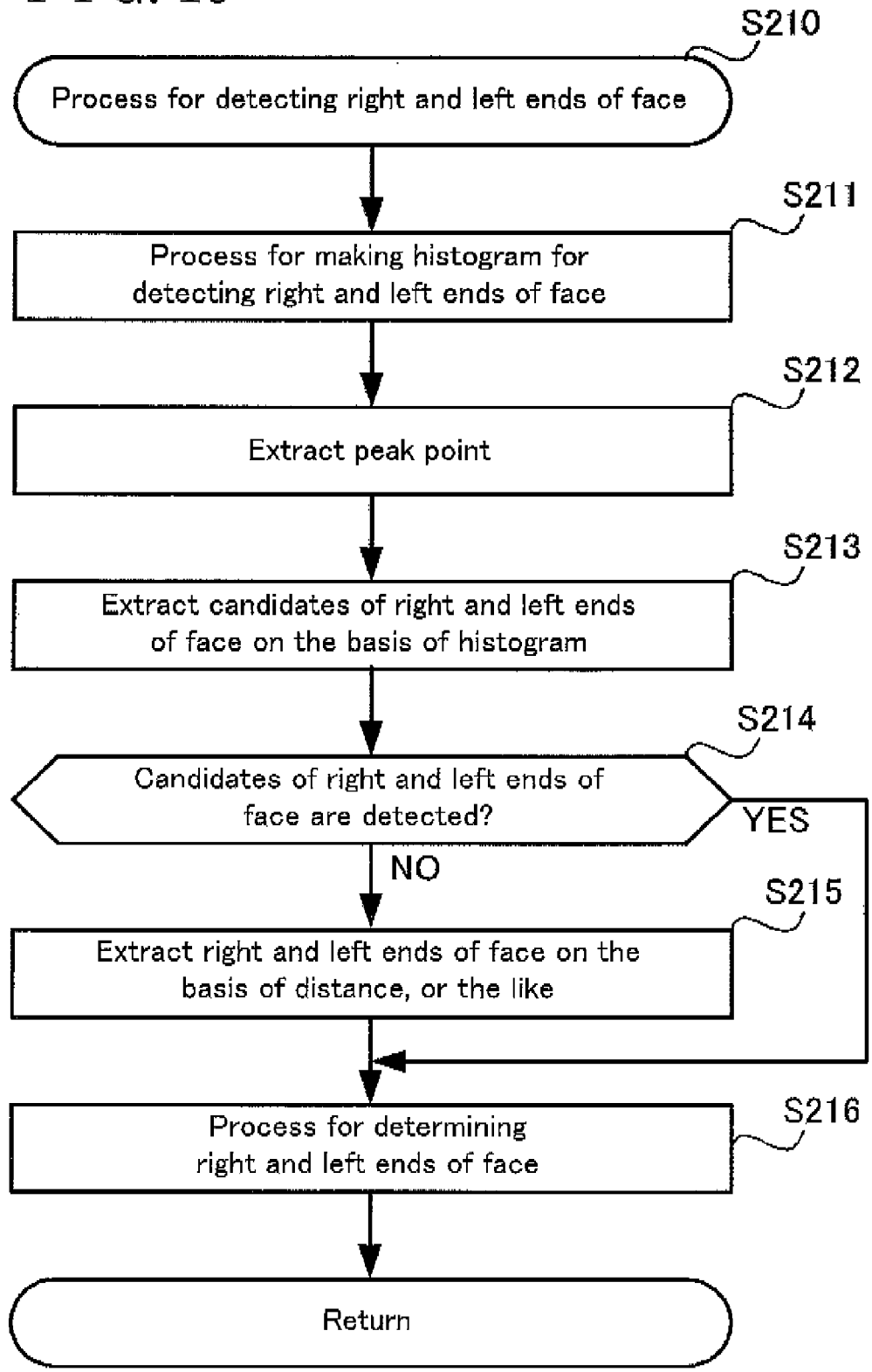
FIG. 10 represents an explanatory diagram illustrating a flowchart of a process for detecting right and left ends of a face in the face-position detecting process.

Details of the process for detecting the right and left ends of the face (S210) will be explained with reference to FIG. 10.

Firstly, the CPU 24 performs a process for making a histogram for detecting the right and left ends of the face (step S211). The CPU 24 makes a histogram by projecting pixel values after the Sobel filter process with use of the vertical-edge detecting Sobel filter in the vertical direction. Specifically, the pixel values are divided into several steps and the pixels are classified into the steps on the basis of the pixel values. A step, in which the largest number of pixels are included, is determined for every x value. An average of the pixel values included in the step is calculated for every x value. A graph of the average relating to the x-coordinate is made. The graph serves as the histogram described above.

The CPU 24 extracts each point, at which a histogram value takes a peak, (hereinafter referred to as a peak point) from the histogram made in the step S211 (step S212).

The CPU 24 extracts peak points, of which the histogram values are equal to or larger than a threshold, from the peak points extracted in the step S212 as a candidate of the right and left ends of the face (step S213).

The CPU 24 judges whether two peak points, of which the histogram values are equal to or larger than the threshold, are extracted as the candidate of the right and left ends of the face as a result of the process in the step S213 (step S214).

When the CPU 24 determines that the two peak points, of which the histogram values are equal to or larger than the threshold, are extracted (step S214; YES), the CPU 24 proceeds the process to step S216. The CPU 24 determines positions, at which the histogram values take the extracted two peak points, as the right and left ends of tie face (step S216).

When the CPU 24 determines that the two peak points, of which the histogram values are equal to or larger than the threshold, are not extracted (step S214; NO), the CPU 24 extracts a combination of two peak points between which a distance is suitable for a width of a face of a human (step S215).

The CPU 24 determines positions, at which the histogram values take the extracted two peak points, as the right and left ends of the face (step S216).

Thus, according to the process for detecting the right and left ends of the face, the right and left ends of the face can be detected in the face image.

Here, the process for detecting the upper and lower ends of the face performed in the step S220 of the face-position detecting process will be explained. Briefly, in the process for detecting the upper and lower ends of the face, the eyelid detection apparatus 50 detects positions of the upper and lower ends of the face in the face image with use of the image, in which the horizontal edge line is emphasized, generated in the preprocess.

Figure 11:
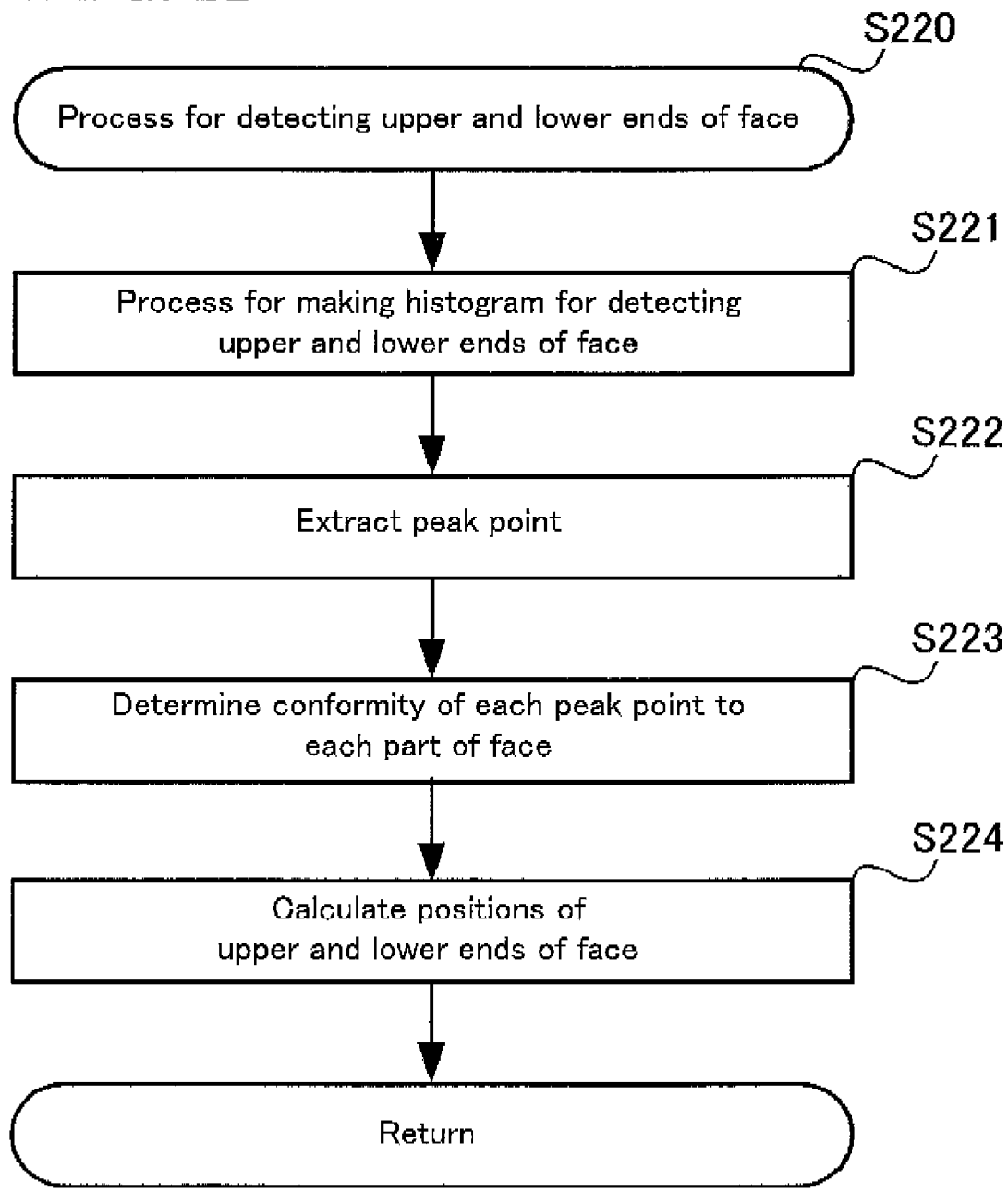
FIG. 11 represents an explanatory diagram illustrating a flowchart of a process for detecting upper and lower ends of the face in the face-position detecting process.

Details of the process for detecting the upper and lower ends of the face (S220) will be explained with reference to FIG. 11.

Firstly, the CPU 24 performs a process for making a histogram for detecting the upper and lower ends of the face (step S221). The CPU 24 makes a histogram by projecting pixel values after the Sobel filter process with use of the horizontal-edge detecting Sobel filter in the horizontal direction. Specifically, the pixel values are divided into several steps and the pixels are classified into the steps on the basis of the pixel values. A step, in which the largest number of pixels are included, is determined for every y value. A average of the pixel values included in the step is calculated for every y value. A graph of the average relating to the y-coordinate is made. The graph serves as the histogram described above.

The CPU 24 extracts each point, at which a histogram value takes a peak, (hereinafter referred to as a peak point) from the histogram made in the step S221 (step S222).

The CPU 24 determines conformity of each peak point to the eyelid, an eyebrow, a mouth, or the like, on the basis of the histogram values of the peak points extracted in the step S222 (step S223).

The CPU 24 calculates the positions of the upper and lower ends of the face in the face image on the basis of each peak point corresponding to the eyelid, the eyebrow, the mouth, or the like, in the step S223 (step S224). For example, a position higher than the detected eyebrow by three pixels is considered as an upper end of the face, and a position lower than the detected mouth by three pixels is considered as a lower end of the face (between the mouth and a jaw).

Thus, according to the process for detecting the upper and lower ends of the face, the positions of the upper and lower ends of the face can be calculated in Me face image.

Here, the eyelid-candidate extracting process performed in the step S300 of the eyelid detection process will be explained. Briefly, in the eyelid-candidate extracting process, the eyelid detection apparatus 50 extracts a certain region, in which the eyelid is assumed to be present, on the basis of the position of the face detected in the face-position detecting process. After that, the eyelid detection apparatus 50 detects the plus edge and the minus edge from the extracted region with use of the horizontal-edge detecting Sobel filter and extracts the edge line pair, which satisfies the formulas (1) to (3) described above, as the eyelid candidate.

Figure 12:
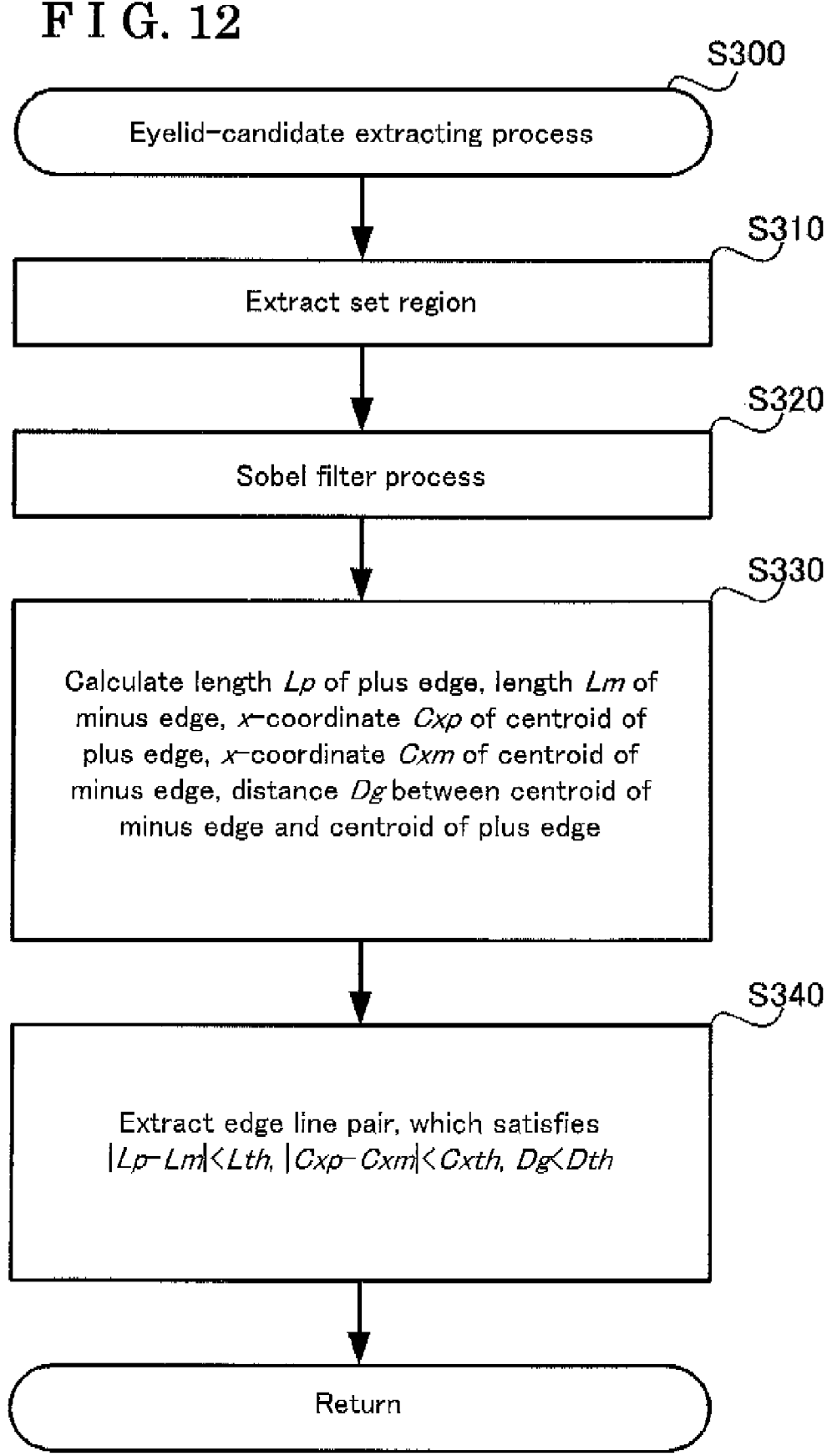
FIG. 12 represents an explanatory diagram illustrating a flowchart of an eyelid-candidate extracting process in the eyelid detection process of the first embodiment.

Details of the eyelid-candidate extracting process (S300) will be explained with reference to FIG. 12.

Firstly, the CPU 24 extracts the image of the region, in which the eyelid is assumed to be present, from each face image stored in the image memory 22 on the basis of the positions of the right and left ends of the face and the upper and lower ends of the face detected in the face-position detecting process and the eyelid-region setting parameters (step S310).

The CPU 24 processes the image of the region extracted in the step S310 with use of the horizontal-edge detecting operator (FIG. 3B) stored in the ROM 23 and distinguishes and extracts a pixel, of which the absolute value of the derivative value is equal to or larger than the eyelid detecting horizontal Sobel threshold, in the image as a part of the horizontal edge line (step S320).

The CPU 24 calculates, for the horizontal edge line extracted in the step S320, the length Lp of the plus edge, the length Lm of the minus edge, the x-coordinate Cxp of the centroid of the plus edge, the x-coordinate Cxm of the centroid of the minus edge, the distance Dg between the centroid of the minus edge and the centroid of the plus edge (step S330).

The CPU 24 extracts the combination of the minus edge and the plus edge, which satisfies the formulas (1) to (3), as the eyelid candidate with use of the parameters calculated in the step S330 (step S340).

Thus, according to the eyelid-candidate extracting process, the combination of the minus edge and the plus edge, which becomes the eyelid candidate, can be extracted in the region, in which the eyelid is assumed to be present.

Here, the eyelid distinguishing process performed in the step S400 of tie eyelid detection process will be explained. Briefly, the eyelid detection apparatus 50 sets regions of the outer or inner corner of the eye at die right and left ends of each eyelid candidate extracted in the eyelid-candidate extracting process, calculates the evaluation values of the outer or inner corner of the eye of the set regions, and distinguishes the eyelid candidate, of which the summation of the calculated left end and right end evaluation values of the outer or inner corner of the eye is largest, as the right or left eyelid. It is possible for the eyelid detection apparatus 50 to distinguish the eyelid candidates, of which the summations of the calculated left end and right end evaluation values of the outer or inner corner of the eye are largest and second largest, as the right and left eyelid.

Figure 13:
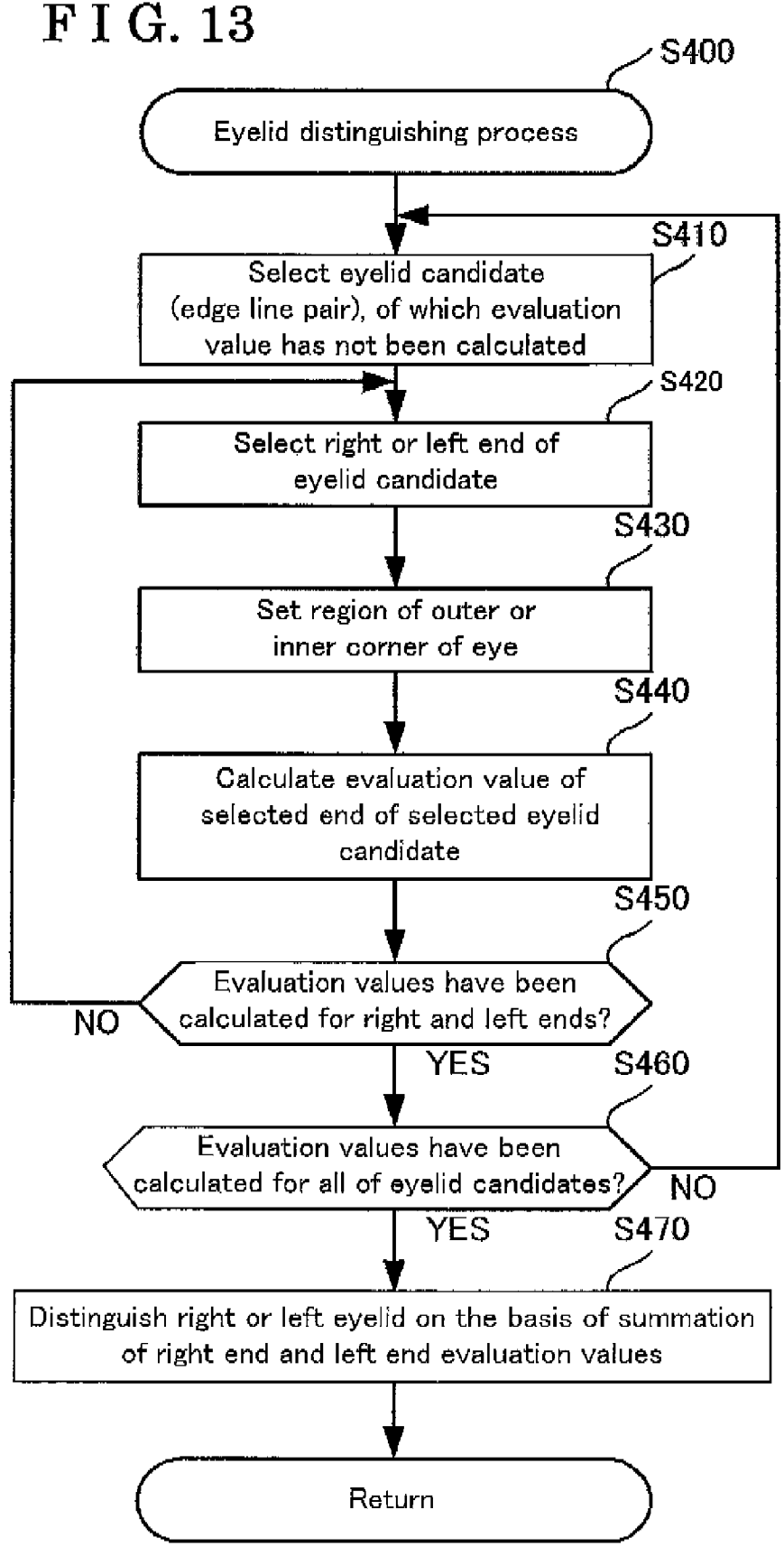
FIG. 13 represents an explanatory diagram illustrating a flowchart of an eyelid distinguishing process in the eyelid detection process of the first embodiment.

Details of the eyelid distinguishing process (S400) will be explained with reference to FIG. 13.

Firstly, the CPU 24 selects an arbitrary eyelid candidate, of which the evaluation value of the outer or inner corner of the eye is not calculated, from the eyelid candidates extracted in the eyelid-candidate extracting process (step S410).

Next, the CPU 24 selects an end, of which the evaluation value of the outer or inner corner of the eye is not calculated, from the right and left ends of the plus edge of the selected eyelid candidate (step S420).

The CPU 24 sets the region of the outer or inner corner of the eye at the selected end of the plus edge of the selected eyelid candidate as a center (step S430).

The CPU 24 locates the pattern of the outer or inner corner of the eye corresponding to the selected end on the original image before the Sobel filter process is performed at a region corresponding to the region of the outer or inner corner of the eye. Next, the CPU 24 calculates the average of the intensity of the pixels in the original image at the part corresponding to the skin part of the pattern and the average of the intensity of the pixels in the original image at the part corresponding to the eye part of the pattern. The CPU 24 calculates the evaluation value of the outer or inner corner of the eye by subtracting the calculated average of the intensity of the pixels in the original image at the part corresponding to the eye part from the calculated average of the intensity of the pixels in the original image at the part corresponding to the skin part (step S440, parameter calculating process).

The CPU 24 judges whether the right end and left end evaluation values of the outer or inner corner of the eye are calculated for the selected eyelid candidate or not (step S450).

When the CPU 24 determines that the right end and left end evaluation values of the outer or inner corner of the eye are not calculated for the selected eyelid candidate (step S450; NO), the CPU 24 goes back to the step S420.

When the CPU 24 determines that the right end and left end evaluation values of the outer or inner corner of the eye are calculated for the selected eyelid candidate (step S450; YES), the CPU 24 judges whether the evaluation values of the outer or inner corner of the eye are calculated for all of the eyelid candidates or not (step S460).

When the CPU 24 determines that the evaluation values of the outer or inner corner of the eye are calculated for all of the eyelid candidates (step S460; NO), the CPU 24 goes back to the step S410.

When the CPU 24 determines that the evaluation values of the outer or inner corner of the eye are calculated for all of the eyelid candidates (step 5460; YES), the CPU 24 calculates a summation of the right end and left end evaluation values of the outer or inner corner of the eye of each eyelid candidate. The CPU 24 determines an eyelid candidate, of which the calculated summation of the right end and left end evaluation values of the outer or inner corner of the eye is largest, as the right or left eyelid (S470, eyelid detecting process). The CPU 24 can determine eyelid candidates, of which the calculated summations of the right end and left end evaluation values of the outer or inner corner of the eye are largest and second largest, as the right and left eyelids.

Thus, according to the eyelid distinguishing process, the evaluation values, which evaluate how the right and left ends of each eyelid candidate resemble the outer or inner corner of the eye, can be calculated and the right and left eyelids can be distinguished on the basis of the evaluation values.

As described above, the eyelid detection apparatus 50 according to the first embodiment detects the face position in plural face images taken at different timings. Then, the eyelid detection apparatus 50 extracts the region, in which the eyelid is assumed to be present, on the basis of the face position and extracts the edge line pair, which becomes the eyelid candidate, from the region. The eyelid detection apparatus 50 determines, in the extracted eyelid candidates (edge line pair), the eyelid candidate, in which the possibility that the outer and inner corners of the eye are included is high, as the eyelid. Accordingly, the eyelid detection apparatus 50 can detect the eyelid correctly within a short time.

(Second embodiment) In the first embodiments when the eyelid detection apparatus 50 distinguishes the eyelid from the eyelid candidates, the eyelid detection apparatus 50 sets the region of the outer or inner corner of the eye, of which an area is as same as that of the pattern of the outer or inner corner of the eye, for each eyelid candidate, applies the pattern of the outer or inner corner of the eye to the region of the outer or inner corner of the eye, and calculates the evaluation value of the outer or inner corner of the eye. However, in the second embodiment, firstly, when the eyelid is distinguished from the eyelid candidates, the eyelid detection apparatus 50 can set a region of the outer or inner corner of the eye, of which an area is larger than that of the pattern of the outer or inner corner of the eye as illustrated in FIG. 14C and FIG. 14D, for each eyelid candidate. Next, as illustrated in FIG. 14D, the eyelid detection apparatus 50 can scan all of the region of the outer or inner corner of the eye by the pattern of the outer or inner corner of the eye, can calculate temporal evaluation values of the outer or inner corner of the eye for the regions scanned by the pattern of the outer or inner corner of the eye, and can determine a maximum temporal evaluation value of the outer or inner corner of the eye as the evaluation value of the outer or inner corner of the eye. Here, the region of the outer or inner corner of the eye in the second embodiment is a region of 21 pixels (horizontal)×11 pixels (vertical) set at the right and left ends of the plus edge of the eyelid candidate as centers.

In the meantime, the configuration of the eyelid detection apparatus according to the second embodiment is similar to the configuration of the eyelid detection apparatus according to the first embodiment. Further, processes other than the eyelid distinguishing process according to the second embodiment are similar to those of the first embodiment.

Figure 15:
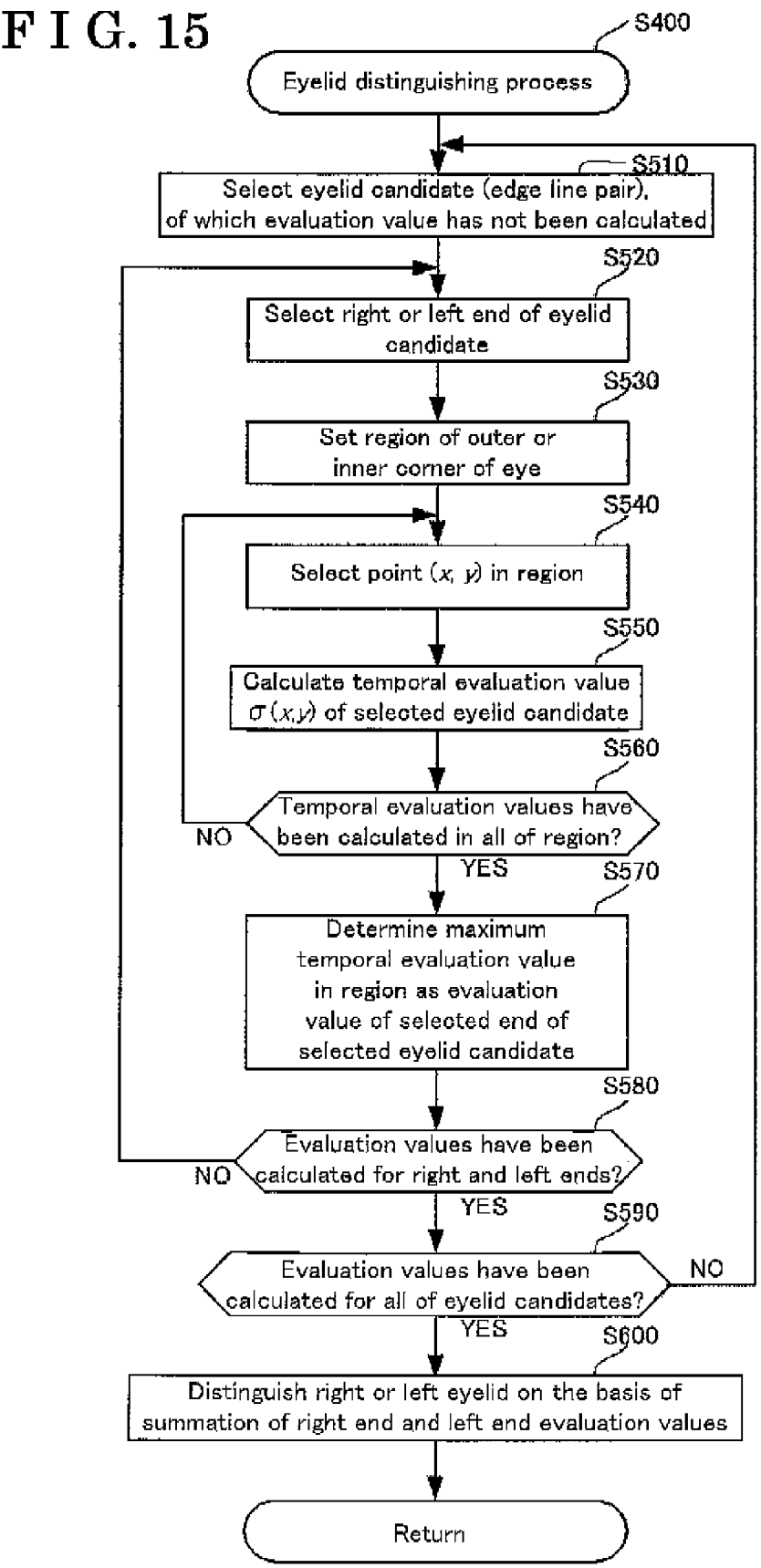
FIG. 15 represents an explanatory diagram illustrating a flowchart of an eyelid distinguishing process in the eyelid detection process of the second embodiment.

Details of the eyelid distinguishing process (S400) according to the second embodiment will be explained with reference to FIG. 15.

Firstly, the CPU 24 selects an arbitrary eyelid candidate, of which the evaluation value of the outer or inner corner of the eye is not calculated, from the eyelid candidates extracted in the eyelid-candidate extracting process (step S510).

Next, the CPU 24 selects an end, of which the evaluation value of the outer or inner corner of the eye is not calculated, from the right and left ends of the plus edge of the selected eyelid candidate (step S520).

The CPU 24 sets the region of the outer or inner corner of the eye at the selected end of the plus edge of the selected eyelid candidate as a center (step S530).

The CPU 24 selects an arbitrary point (x, y) in the set region of the outer or inner corner of the eye (step S540).

The CPU 24 locates the pattern of the outer or inner corner of the eye of the selected end on the original image before the Sobel filter process at the arbitrary point (x, y) of the region of the outer or inner corner of the eye as a base point. Next, the CPU 24 calculates the average of the intensity of the pixels in the original image at the part corresponding to the skin part of the pattern and the average of the intensity of the pixels in the original image at the part corresponding to the eye part of the pattern. The CPU 24 calculates the temporal evaluation value σ (x, y) (difference) of the outer or inner corner of the eye by subtracting the calculated average of the intensity of the pixels in the original image at the part corresponding to the eye part from the calculated average of the intensity of the pixels in the original image at the part corresponding to the skin part (step S550 difference calculating process).

The CPU 24 judges whether the temporal evaluation values plural differences) of the outer or inner corner of the eye are calculated for all of the region of the outer or inner corner of the eye or not (step S560).

When the CPU 24 determines that the temporal evaluation values of the outer or inner corer of the eye are not calculated for all of the region of the outer or inner corner of the eye (step S560; NO), the CPU 24 goes back to the step S540.

When the CPU 24 determines that the temporal evaluation values of the outer or inner corner of the eye are calculated for all of the region of the outer or inner corner of the eye (step S560; YES), the CPU 24 determines the maximum calculated temporal evaluation value (maximum difference) of the outer or inner corner of the eye as the evaluation value of the outer or inner corner of be eye of the selected end of the selected eyelid candidate (step S570, parameter calculating process).

The CPU 24 judges whether the right end and left end evaluation values of the outer or inner corner of the eye are calculated for the selected eyelid candidate or not (step S580).

When the CPU 24 determines that the right end and left end evaluation values of the outer or inner corner of the eye are not calculated for the selected eyelid candidate (step S580; NO), the CPU 24 goes back to the step S520.

When the CPU 24 determines that the right end and left end evaluation values of the outer or inner corner of the eye are calculated for the selected eyelid candidate (step S580; YES), the CPU 24 judges whether the evaluation values of the outer or inner corner of the eye are calculated for all of the eyelid candidates or not (step S590), When the CPU 24 determines that the evaluation values of the outer or inner corner of the eye are not calculated for all of the eyelid candidates (step 5590; NO), the CPU 24 goes back to the step S510.

When the CPU 24 determines that the evaluation values of the outer or inner corner of the eye are calculated for all of the eyelid candidates (step S590;YES), the CPU 24 calculates the summation of the right end and left end evaluation values of the outer or inner corner of the eye of each eyelid candidate. The CPU 24 determines an eyelid candidate, of which the calculated summation of the right end and left end evaluation values of the outer or inner corner of the eye is largest as the right or left eyelid (step S600, eyelid detecting process). The CPU 24 can determine eyelid candidates, of which the calculated summation of the right end and left end evaluation values of the outer or inner corner of the eye are largest and second largest, as the right and left eyelids.

Thus, according to the eyelid distinguishing process of the second embodiment, parts, which resemble the outer and inner corners of the eye, can be extracted from the region neat the right and left ends of each eyelid candidate, the evaluation values of the extracted parts can be calculated, and the right and left eyelids can be distinguished on the basis of the evaluation values.

As described above, the eyelid detection apparatus 50 according to the second embodiment detects the face position from the plural face images taken at different timings. Then, the eyelid detection apparatus 50 extracts the region, in which the eyelid is assumed to be present, on the basis of the face position and extracts the edge line pair, which becomes the eyelid candidate, from the region. The eyelid detection apparatus 50 sets the region of the outer or inner corner of the eye, of which the area is larger than that of tie pattern of the outer or inner corner of the eye, for the right and left ends of each extracted eyelid candidate (edge line pair). Next, the eyelid detection apparatus 50 scans all of the region of the outer or inner corner of the eye by the pattern of the outer or inner corner of the eyes calculates the temporal evaluation values of the outer or inner corner of the eye for the regions scanned by the pattern of the outer or inner corner of the eye, determines the maximum temporal evaluation value of the outer or inner corner of the eye as the evaluation value of the outer or inner corer of the eye, and distinguishes the right or left eyelid on the basis of the evaluation values of the outer or inner corner of the eye. Accordingly, the eyelid detection apparatus 50 can extract parts, which resemble the outer and inner corners of the eye mostly, from the eyelid candidates. Therefore, the eyelid detection apparatus 50 can detect the eyelid correctly within a short time.

In the meantime, configurations of the eyelid detection apparatus are not limited to the embodiments described above. Various kinds of modifications and applications can be made for the eyelid detection apparatus.

In the first and second embodiments, the computer 14 performs the eyelid detection process for the motion image of the face of the subject taken by the camera 10. However, in an application example, a motion image of the face of the subject taken by an external device other than the camera 10 can be stored in the image memory 22 and the eyelid detection process can be performed for the motion image. Further, the eyelid detection process can be performed for plural face images.

Further, in the first and second embodiments, in the face-position detecting process (S200), the Sobel filter process is executed for the face image and the face position is detected from the histogram on the basis of the pixel value. However, in an application example, as described in JP2004-310396A, the face position can be detected by temporally differentiating each pixel included by the taken image, projecting the temporally differentiated image in a vertical direction to make a histogram, summing the histograms of an edge-extracted image and the temporally differentiated image, and determining high peak values of the summed histogram as both ends of the face.

Further, in the face-position detecting process (S200), a template matching method can be utilized. The face position can be detected by matching a preliminarily registered template to the face image.

Further, in the embodiment, a part, in which the possibility that the part includes the outer and inner corners of the eye is high, is distinguished as the eyelid. However, a part, in which a possibility that the part includes either one of the outer and inner corners of the eye is high, can be distinguished as the eyelid.

Further, in the embodiment, a method for extracting the horizontal edge lines with use of the Sobel filter is utilized for detecting lines corresponding to the upper and lower eyelids in the face image. However, other method can be utilized for detecting an edge. For example, an edge can be detected with use of a MAX-MIN filter.

Further, in the embodiment, the regions of the outer or inner corner of the eye are set at right and left ends of the lower eyelid candidate (plus edge) as centers. However, the regions of the outer or inner corner of the eye can be set at points other than the right and left ends of the plus edge as centers. For example, the region of the outer or inner corner of the eye can be set at a part, at which a proximity of the end of the plus edge accounts for approximately two thirds of the region and a blank accounts for one third of the region.

In the meantime, the eyelid detection apparatus can be carried out not only by a dedicated system but also by a general computer system. For example, the program for executing the operations described above can be stored in a recording medium (flexible disk, CD-ROM, DVD-ROM, or the like), which can be read by a computer system, and can be distributed. The eyelid detection apparatus can be configured from a computer system, which is configured so that the face image can be input, and in which the program is installed. Further, the program can be stored in a storage of a server apparatus on a communication network, such as an internet, or the like. The eyelid detection apparatus can be configured from a general computer system, in which the program is downloaded, or the like.

Further, in a case where functions described above are shared by an operating system (OS) and an application, or in a case where the functions are carried out with cooperation of the OS and the application, it is possible to store an application program in the recording medium or the storage.

Further, it is possible to overlap the program on a carrier wave and to deliver the program through the communication network. For example, the program can be stored in the server on the communication network and the program can be delivered through the network. Then, the eyelid detection apparatus can be configured by starting the program and executing the program under the control of the OS, in the same way as other application programs.

The eyelid detection apparatus, the eyelid detection method and the program therefor detects, for example, the eye of the driver, or the like, who drives a moving object, for example, a vehicle, or the like.

According to the embodiments, the CPU 24 calculates the evaluation value, which indicates the possibility that the eyelid region of the image stored in the image memory 22, the eyelid region including both ends of the line which is the candidate of the lower eyelid extracted by the CPU 24, includes at least one of the outer and inner corners of the eye.

According to the embodiments, the CPU 24 calculates the average of intensity of the plural pixels in the eyelid region of the image stored in the image memory 22, the eyelid region including both ends of the line which is the candidate of the lower eyelid extracted by the CPU 24, and calculates the evaluation value which indicates the possibility that the eyelid region of the image stored in the image memory 22, the eyelid region including both ends of the line which is the candidate of the lower eyelid extracted by the CPU 24, includes at least one of the outer and inner corners of the eye on the basis of the calculated average of the intensity of the plural pixels.

According to the embodiments, the eyelid detection apparatus 50 includes the ROM 23 for storing the pattern of the outer or inner corner of the eye which represents the part corresponding to the skin part and the part corresponding to the eye part, the pattern of which the area is equal to that of the eyelid region including the both ends of the line. The CPU 24 calculates a difference between the average of intensity of the plural pixels of the part of the image stored in the image memory 22, the part corresponding to the skin part which is represented by the pattern stored in the ROM 23, and the average of intensity of the plural pixels of the part of the image stored in the image memory, the part corresponding to the eye part which is represented by the pattern stored in the pattern storing means, and detects the eyelid on the basis of the difference.

According to the second embodiment, the eyelid detection apparatus 50 includes the ROM 23 for storing the pattern of the outer or inner corner of the eye which represents the part corresponding to the skin part and the part corresponding to the eye part, the pattern of which the area is smaller than the eyelid region including the both ends of the line. The CPU 24 applies the pattern stored in the image memory 22 to the part of the eyelid region including the both ends of the line to calculate the temporal evaluation value, in other words, the difference between the average of intensity of the plural pixels of the part of the image stored in the image memory 22, the part corresponding to the skin part represented by the pattern, and the average of intensity of the plural pixels of the part of the image stored in the image memory 22, the part corresponding to the eye part represented by the pattern stored in the ROM 23, determines the largest temporal evaluation value of the temporal evaluation values calculated by the CPU 24 by scanning the eyelid region including the both ends of the line as the evaluation value, and detects the eyelid on the basis of the evaluation value.

According to the embodiments, the CPU 24 detects the right and left eyelids of the subject.

According to the embodiments, eyelid candidates, which have largest and second largest evaluation values calculated by the CPU 24, are detected as the right and left eyelids by the CPU 24.

According to the embodiments, the eyelid detection method includes processes of processing the face image to extract the pair of lines, which becomes the candidate of the combination of the upper eyelid and the lower eyelid S300, calculating the evaluation value which indicates the possibility that the extracted pair of lines which becomes the candidate of the combination of the upper eyelid and the lower eyelid, includes at least one of the outer or inner corners of the eye S440, S570, and detecting the position of the eyelid of the subject on the basis of the calculated evaluation value S470, S600.

According to the embodiments, a program instructs the computer 14 to store the image of the face of the subject, to process the image stored in the image memory 22 and to extract the pair of lines which becomes the candidate of the combination of the line corresponding to the upper eyelid and the line corresponding to the lower eyelid, to calculate the evaluation value which indicates possibility that the part of the image stored in the CPU 24, the part corresponding to the pair of lines extracted by the CPU 24, includes at least one of the outer or inner corner of the eye, and to detect the position of the eyelid of the subject on the basis of the evaluation value calculated by the CPU 24.

According to the embodiments of the present invention, the eyelid detection apparatus, the eyelid detection method and the program therefor, which can detect the eyelid by minimal calculations, can be provided.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. An eyelid detection apparatus, comprising:
 a face-image storing means for storing an image of a face of a subject;
 an eyelid-candidate extracting means for processing the image stored in the face-image storing means and extracting a pair of lines, which becomes a candidate of a combination of a line corresponding to an upper eyelid and a line corresponding to a lower eyelid;
 a parameter calculating means for calculating an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculating a parameter, which indicates a possibility that the predetermined part of the image including the both ends of the line includes at least one of an outer corner and an inner corner of an eye on the basis of the calculated average value of the intensity of the plural pixels;
 an eyelid detecting means for detecting a position of an eyelid of the subject on the basis of the parameter calculated by the parameter calculating means; and
 a pattern storing means for storing a pattern which represents a skin region corresponding to a skin part and an eye region corresponding to an eye part, within an area, which is equal to that of the predetermined part including the both ends of the line, wherein
 the parameter calculating means calculates a difference between an average value of intensity of plural pixels of a part of the image stored in the face-image storing means corresponding to the skin region, which is represented by the pattern stored in the pattern storing means, and an average value of intensity of plural pixels of a part of the image stored in the face- image storing means corresponding to the eye region, which is represented by the pattern stored in the pattern storing means, and wherein the eyelid detecting means detects right and left eyelids on the basis of the difference.

2. An eyelid detection apparatus, comprising:

a face-image storing means for storing an image of a face of a subject;

an eyelid-candidate extracting means for processing the image stored in the face-image storing means and extracting a pair of lines, which becomes a candidate of a combination of a line corresponding to an upper eyelid and a line corresponding to a lower eyelid;

a parameter calculating means for calculating an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculates a parameter, which indicates a possibility that the predetermined part of the image including the both ends of the line includes at least one of an outer corner and an inner corner of an eye on the basis of the calculated average value of the intensity of the plural pixels;

an eyelid detecting means for detecting a position of an eyelid of the subject on the basis of the parameter calculated by the parameter calculating means; and a pattern storing means for storing a pattern which represents a skin region corresponding to a skin part and an eye region corresponding to an eye part, within an area, which is narrower than that of the predetermined part including the both ends of the line, wherein the parameter calculating means includes a difference calculating means for relating the pattern stored by the pattern storing means to a portion of the predetermined part including the both ends of the line and calculating a difference between an average value of intensity of plural pixels of a part of the image stored in the face-image storing means corresponding to the skin region, which is represented by the pattern stored in the pattern storing means, and an average value of intensity of plural pixels of a part of the image stored in the face-image storing means corresponding to the eye region, which is represented by the pattern stored in the pattern storing means, the difference calculating means scans the predetermined part including the both ends of the line and sets a greatest difference among the calculated plural differences as a maximum difference value, and the eyelid detecting means detects right and left eyelids on the basis of the maximum difference value.

3. An eyelid detection method, which is executed by an eyelid detection apparatus comprising a face-image storing means for storing an image of a face of a subject, an eyelid-candidate extracting means, a parameter calculating means, an eyelid detecting means and a pattern storing means, the eyelid detection method comprising processes of:

an eyelid-candidate extracting process where the eyelid-candidate extracting means processes the image stored in the face-image storing means and extracts a pair of lines, which becomes a candidate of a combination of a line corresponding to an upper eyelid and a line corresponding to a lower eyelid;

a parameter calculating process where the parameter calculating means calculates an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculates a parameter, which indicates a possibility that the predetermined part of the image including the both ends of the line includes at least one of an outer corner and an inner corner of an eye on the basis of the calculated average value of the intensity of the plural pixels; and an eyelid detecting process where the eyelid detecting means detects a position of an eyelid of the subject on the basis of the parameter calculated by the parameter calculating means; wherein the pattern storing means stores a pattern which represents a skin region corresponding to a skin part and an eye region corresponding to an eye part, within an area, which is equal to that of the predetermined part including the both ends of the line, the parameter calculating means calculates a difference between an average value of intensity of plural pixels of a part of the image stored in the face-image storing means corresponding to the skin region, which is represented by the pattern stored in the pattern storing means, and an average value of intensity of plural pixels of a part of the image stored in the face-image storing means corresponding to the eye region, which is represented by the pattern stored in the pattern storing means, in the parameter calculating process, and the eyelid detecting means detects right and left eyelids on the basis of the difference in the eyelid detecting process.

4. An eyelid detection method, which is executed by an eyelid detection apparatus comprising a face-image storing means for storing an image of a face of a subject, an eyelid-candidate extracting means, a parameter calculating means, an eyelid detecting means and a pattern storing means, the eyelid detection method comprising processes of:

an eyelid-candidate extracting process where the eyelid-candidate extracting means processes the image stored in the face-image storing means and extracts a pair of lines, which becomes a candidate of a combination of a line corresponding to an upper eyelid and a line corresponding to a lower eyelid;

a parameter calculating process where the parameter calculating means calculates an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculates a parameter, which indicates a possibility that the predetermined part of the image including the both ends of the line includes at least one of an outer corner and an inner corner of an eye on the basis of the calculated average value of the intensity of the plural pixels; and an eyelid detecting process where the eyelid detecting means detects a position of an eyelid of the subject on the basis of the parameter calculated by the parameter calculating means; wherein the pattern storing means stores a pattern which represents a skin region corresponding to a skin part and an eye region corresponding to an eye part, within an area, which is narrower than that of the predetermined part including the both ends of the line, the parameter calculating means relates the pattern stored in the pattern storing means to a portion of the predetermined part including the both ends of the line, and calculates a difference between an average value of intensity of plural pixels of a part of the image stored in the face-image storing means corresponding to the skin region, which is represented by the pattern stored in the pattern storing means, and an average value of intensity of plural pixels of a part of the image stored in the face-image storing means corresponding to the eye region, which is represented by the pattern stored in the pattern storing means, in the parameter calculating process, the difference calculating means scans the predetermined part including the both ends of the line and sets a greatest difference among the calculated plural differences as a maximum difference value, and the eyelid detecting means detects right and left eyelids on the basis of the maximum difference value in the eyelid detecting process.

5. A non-transitory computer-readable medium including a program for instructing a computer to function as:

a face-image storing means for storing an image of a face of a subject;

an eyelid-candidate extracting means for processing the image stored in the face-image storing means and extracting a pair of lines which becomes a candidate of a combination of a line corresponding to an upper eyelid and a line corresponding to a lower eyelid;

a parameter calculating means for calculating an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculates a parameter, which indicates a possibility that the predetermined part of the image including the both ends of the line includes at least one of an outer corner and an inner corner of an eye on the basis of the calculated average value of the intensity of the plural pixels;

an eyelid detecting means for detecting a position of an eyelid of the subject on the basis of the parameter calculated by the parameter calculating means; and a pattern storing means for storing a pattern which represents a skin region corresponding to a skin part and an eye region corresponding to an eye part, within an area, which is equal to that of the predetermined part including the both ends of the line, wherein the parameter calculating means calculates a difference between an average value of intensity of plural pixels of a part of the image stored in the face-image storing means corresponding to the skin region, which is represented by the pattern stored in the pattern storing means, and an average value of intensity of plural pixels of a part of the image stored in the face-image storing means corresponding to the eye region, which is represented by the pattern stored in the pattern storing means, in the parameter calculating process, and the eyelid detecting means detects right and left eyelids on the basis of the difference.

6. A non-transitory computer-readable medium including a program for instructing a computer to function as:

a face-image storing means for storing an image of a face of a subject;

an eyelid-candidate extracting means for processing the image stored in the face-image storing means and extracting a pair of lines which becomes a candidate of a combination of a line corresponding to an upper eyelid and a line corresponding to a lower eyelid;

a parameter calculating means for calculating an average value of intensity of plural pixels in a predetermined part of the image, which is stored within the face-image storing means, including both ends of the line, which is one of the pair of the candidate lines extracted by the eyelid-candidate extracting means and corresponding to the lower eyelid, and calculates a parameter, which indicates a possibility that the predetermined part of the image including the both ends of the line includes at least one of an outer corner and an inner corner of an eye on the basis of the calculated average value of the intensity of the plural pixels;

an eyelid detecting means for detecting a position of an eyelid of the subject on the basis of the parameter calculated by the parameter calculating means; and a pattern storing means for storing a pattern which represents a skin region corresponding to a skin part and an eye region corresponding to an eye part, within an area, which is narrower than that of the predetermined part including the both ends of the line, wherein the parameter calculating means includes a difference calculating means for relating the pattern stored in the pattern storing means to a portion of the predetermined part including the both ends of the line, and calculating a difference between an average value of intensity of plural pixels of a part of the image stored in the face-image storing means corresponding to the skin region, which is represented by the pattern stored in the pattern storing means, and an average value of intensity of plural pixels of a part of the image stored in the face-image storing means corresponding to the eye region, which is represented by the pattern stored in the pattern storing means, in the parameter calculating process, and the difference calculating means scans the predetermined part including the both ends of the line and sets a greatest difference among the calculated plural differences as a maximum difference value, and the eyelid detecting means detects right and left eyelids on the basis of the maximum difference value.

* * * * *